(12) United States Patent
Golz-Berner et al.

(10) Patent No.: US 6,517,818 B1
(45) Date of Patent: Feb. 11, 2003

(54) LIP OR CARE STICK WHICH CONTAINS VITAMINS

(75) Inventors: Karin Golz-Berner, Monaco (DE); Leonhard Zastrow, Monaco (DE); Benoit Joly, Saint Laurent du Var (FR)

(73) Assignee: Coty B.V. (NL)

( * ) Notice: Subject to any disclaimer, the term of this patent is extended or adjusted under 35 U.S.C. 154(b) by 0 days.

(21) Appl. No.: 09/763,595

(22) PCT Filed: Nov. 4, 1999

(86) PCT No.: PCT/DE99/03585

§ 371 (c)(1),
(2), (4) Date: Feb. 22, 2001

(87) PCT Pub. No.: WO00/25733

PCT Pub. Date: May 11, 2000

(30) Foreign Application Priority Data

Jan. 4, 1998 (DE) .......................................... 198 52 196

(51) Int. Cl.$^7$ ............................. A61K 6/00; A61K 7/00; A61K 7/025

(52) U.S. Cl. .......................................... 424/64; 424/401

(58) Field of Search ............................ 424/64, 401, 450

(56) References Cited

U.S. PATENT DOCUMENTS 5,843,407 A * 12/1998 El-Nokaly et al. ............ 424/64

* cited by examiner

*Primary Examiner*—Thurman K. Page
*Assistant Examiner*—S. Howard
(74) *Attorney, Agent, or Firm*—Pendorf & Cutliff

(57) ABSTRACT

The invention relates to a lip or care stick which contains vitamins and which is used for cosmetic applications. The stick contains an outer complex comprised of a cellulose derivative having a particle size ranging from 0.5 to 100 μm, and is comprised of a phospholipid and of an α-tocopheral ester. The proportion of the complex is equal to 0.5 and 40 wt. %, with regard to the total mass. The stick also contains cosmetically conventional fats, waxes and additive which have a proportion ranging from 99.5 to 60 wt. % α-tocopheral is stabilized with regard to UV-filters, can also be dissolved in the form of the complex by moisture and can be absorbed and processed as a vitamin by the body.

15 Claims, No Drawings

LIP OR CARE STICK WHICH CONTAINS VITAMINS

BACKGROUND OF THE INVENTION

The invention relates to a lip or care stick which contains vitamins and which is used for cosmetic applications. The term lipstick will used herein to refer to both a colored lipstick and a lip care stick such as a chap stick.

DESCRIPTION OF THE RELATED ART

It is known from DE 38 206 93 A1 that in topic preparations free tocopherols can be stabilised in the presence of sun-blockers by adding ascorbic acids of $C_{11}$–$C_{18}$ fatty acids and citric acid esters of partial glycerides of $C_{12}$–$C_{20}$ fatty acids.

Further, it is known from US-A-4954332 that tocopherols and vitamin C decompose in the presence of UV filters, and steroid and non-steroid anti-inflammation agents are added to prevent decomposition.

Further, a number of lipstick products are known which contain tocopherol additives as anti-oxidants (e.g. US-A-4699780).

SUMMARY OF THE INVENTION

It is an object of the invention to develop new lip and care sticks containing stabilised tocopherols.

It is another object of the invention to keep the tocopherol content at a stable level when used together with common chemical sun-blockers.

DETAILED DESCRIPTION OF THE INVENTION

According to the invention, there are provided lip or care sticks on a wax base in which the cosmetic stick substance contains an addition complex comprised of a cellulose derivative comprising carboxymethyl cellulose, methyl cellulose, hydroxymethyl cellulose, hydroxypropyl cellulose and hydroxypropylmethyl cellulose having a particle size between 0.5 and 100 $\mu$m, a phospholipid and an α-tocopherol ester comprising tocopheryl acetate, tocopheryl succinate, tocopheryl propionate, tocopheryl oleate, tocopheryl linolate, tocopheryl sorbate, the proportion of said complex being 0.5 to 40 wt. % relative to the overall weight, together with cosmetically conventional fats, waxes and additives having a proportion of 99.5 to 60 wt. %.

It was found out that the addition complexes of tocopherol, a phospholipid and cellulose derivatives represent a form in which the cellulose complexes are dissolved by humidity and, together with the settled tocopherols, are taken in by the body of the user wherein the body can process the tocopherol as a vitamin.

A preferred α-tocopherol ester is α-tocopheryl acetate.

Preferably, the proportion of the addition complex ranges between 2 and 30 wt. %, preferably from 5 to 25 wt. % relative to the overall weight. Other preferred proportions range between 8 and 28 wt. %, particularly from 8 to 18 wt. %.

Suitable phospholipids are phosphatidylcholine, phosphatidylethanolamine, phosphatidylinositol and phosphatidylserine and mixtures thereof, the most preferred of which is phosphatidylcholine. The phospholipid proportion may range between 0.01 and 5 wt. %, preferably from 0.05 to 3 wt. % relative to the total composition.

Other additives are selected among oil-soluble UVB filters including 4-aminobenzoic acid derivatives such as 4-(dimethylamino) benzoic acid(2-ethylhexyl)ester; cinnamic acid esters such as 4-methoxy cinnamic acid(2-ethylhexyl)ester, benzophenone derivatives such as 2-hydroxy-4-methoxybenzophenone; 3-benzylidene camphor derivatives such as 3-benzylidene camphor. Preferred UV filters are benzophenone-3, butyl methoxybenzoylmethane, octyl methoxycinnamate, octyl salicylate, 4-methyl benzylidene camphor, homosalate and octyl dimethyl PABA.

It was found out that the proportion of these UV filters does not have any adverse effect onto the tocopherol proportion, i.e. the tocopherol proportion remains essentially stable without any prior art decomposition processes occurring.

The organic UV filters may range between 2 and 15 wt. % of the overall weight of the stick.

Inorganic UV filters may be selected as further additives, such as $TiO_2$, $SiO_2$, ZnO and mixtures thereof, the proportions of which have to be adapted to obtain the desired colour of the stick. $TiO_2$ proportions between 1 and 4 wt. % are advantageous.

The waxes may be selected among carnauba wax, candelilla wax, ozokerite, beeswax, montan wax, wool wax, ceresine, micro-waxes, paraffin waxes, petrolatum.

Further additives are, for example, selected among castor oil, paraffin oil, myristyl lactate, isopropyl myristate, isopropyl lanolate, isopropyl palmitate, p-hydroxybenzoic acid propyl ester.

Other suitable oils are, for example, mineral oils, hydrogenated polyisobutene, polyisoprene, squalane, tridecyltrimellitate, trimethylpropane triisostearate, isodecylcitrate, neopentyl glycol diheptanoate, PPG-15-stearyl ether, calendula oil, jojoba oil, avocado oil, macadamia nut oil, olive oil or a mixture thereof. Depending upon the oils selected, the cosmetic properties of the solid composition, such as softness, hardness, spreading effect, are affected.

In order to improve the hardness and stability of the sticks according to the invention, polymers or copolymers are contained therein, such as, for example, hydrogenated styrene/methyl styrene/inden copolymers, e.g. Régalite R101® by Hercules; copolymers of vinylpyrrolidone and long-chain α-olefines such as Antaron V220®, Antaron V216®, Unimer U15®; salts of fatty acid esters such as sodium isostearoyl lactylate (Pationic ISL® by Rita Corp.); and PEG-120 methyl glucose dioleate (e.g. glucamate DOE 120®);as well as mixtures thereof, and of natural rubbers such as polyisoprene.

Likewise preferred are hydrogenated styrene/methyl styrene/inden copolymers as they reduce the breaking strength of sticks. Further, hydrogenated hydrocarbon resins ensure a better mouldability and filling ability of the composition into lipstick or thin stick moulds.

Other additives or agents in the cosmetic compositions may include vitamins, e.g. vitamin A or vitamin A derivatives; dyed plant extracts such as fat-soluble gardenia extract, fat-soluble carrot extract, paprika LS extract, β-carotene, lithospermum extract.

The addition of fragrance substances is of interest as well. Perfume proportions may be added to the sticks according to the invention, mostly dissolved in alcohols and as a concentrate.

Further, the addition of dyes and pigments to the sticks according to the invention is of particular interest. All known organic dyes and inorganic pigments common to the cosmetic industry may be used. It has to be noted that for maintaining a possible transparency of a composition it is required to dye said composition using organic oil-soluble dyes while inorganic pigments may be used for translucent or more turbid compositions as well.

The organic oil-soluble dyes may be added problem-free to the composition. Advantageously, inorganic pigments are applied by grinding the pigment or pigment mixture together with an oil and then adding it to the composition. Small quantities of pigments, approximately in a proportion between 0.1 and 0.3 wt. %, result in coloured, nearly transparent solid compositions provided that appropriate basic substances such as lanosterine are used. In case of larger pigment quantities, approximately between 3 and 4 wt. %, the composition is turbid or opaque. Hence, the formulation of lipsticks, lip gloss or foundations is possible, also representing specific embodiments of the invention, in which the pigment proportions may be up to 8 wt. %.

Pigments, pigment mixtures or powders with a pigment-like effect, also including those with a pearl-gloss effect, may include, for example, iron oxides, titanium (di)oxide, mica, kaolin, French chalk, mica-titanium oxide, mica-titananium oxide-iron oxide, bismuth oxychloride, nylon beads, ceramic beads, expanded and non-expanded synthetic polymer powders, powdery natural organic compounds such as milled solid algae, encapsulated and non-encapsulated cereal starches and mica-titanium oxide-organic dye.

Another specific feature of the invention is that the composition is free of an aqueous phase, i.e. it does not contain separately added water which would have to be understood as an independent phase. At most, the composition contains such small amounts of water which are brought in because they are physically bound to some additives. This proportion is, however, considerably less than 5 wt. %. Thus, the compositions according to the invention differ clearly from preparations containing cellulose derivatives as thickeners in aqueous solutions or emulsions.

Further, it was found out that α-tocopheryl acetate has a surprisingly excellent stability at the lipstick processing temperature which, due to the melting of the waxes, ranges between 70 and 80° C. and at which temperature the other additives are added, too. The α-tocopheryl acetate is a common commercial product (CWS/F by Hoffmann-La Roche, Switzerland).

In addition to the α-tocopherol present in the addition complex with the cellulose derivative, the mixture of other additives may contain a proportion of α-tocopherol as radical scavenger.

Another advantageous embodiment of the invention contains mineral salts among the additives. These mineral salts may represent a proportion comparable to that of trace elements in foodstuff or mineral waters, wherein the proportion is related to the overall weight of the lipstick. Such mineral salts include Na, K, Ca, P, Fe, I, Cu, Co, Mo and Zn as well as Cl and $SO_4$. The total proportion of such trace elements ranges mostly between 1 and 2.5 g/l and may be present in this proportion in the lipstick substance according to the invention, too.

The production of the solid compositions according to the invention is performed by firstly dispersing the cellulose derivative in an oil phase while adding phospholipids such as phosphatidylcholine at approximately 40–55° C. under stirring at 200–400 rpm. Then, α-tocopherol ester in powdery form is added, and after increasing the temperature to approx. 60–65° C. homogenisation takes place at approx. 10,000 to 15,000 rpm. Thereafter, further cosmetic agents or other additives are added under stirring and at temperatures appropriate to these substances and known to a person skilled in the art. At temperatures between approximately 60 and 80° C., the homogenous mixture which has been vented before in the usual way by slow stirring is poured into appropriate moulds and cooled down.

The invention also relates to a lip or care stick containing vitamins according to the features specified in claim 1, being produced according to the aforementioned method, wherein the production is performed without adding an aqueous phase.

If resin-like polymers and copolymers are added as additives the melting point of which is higher, it is advantageous to add such substances by melting to the composition.

Now the invention is explained in more detail using examples. All numerical values refer to weight percent unless specified otherwise.

EXAMPLE 1

| Lipstick I | |
|---|---|
| Caprylic/capric/isostearic/adipic triglyceride | 7.0 |
| Isopropyl palmitate | 11.0 |
| Candelilla wax | 6.5 |
| Ozokerite wax | 2.5 |
| Carnauba wax | 0.5 |
| Beeswax | 4.0 |
| Lanoline | 7.0 |
| Castor oil | ad 100 |
| Benzophenone-3 | 7.0 |
| Butyl methoxybenzoylmethane | 3.0 |
| α-tocopherol/cellulose complex | 16 |
| Phosphatidylcholine | 1.4 |
| Glycerol | 3.0 |
| Pigments | 7.0 |
| Fragrances | 1.0 |

Carboxymethyl cellulose is dispersed in castor oil while adding phosphatidylcholine under stirring at 360 rpm at approx. 40° C. Then, α-tocopherol acetate in powdery form (1.2 wt. % relative to the overall composition) is added. After increasing the temperature to approx. 62° C., homogenisation takes place at approx. 12,000 rpm. The waxes are molten at approx. 85° C., cooled down to approx. 75° C. and vented in a vacuum. The remaining components are, one after the other, added to the oil phase with the complex at approx. 55° C. and homogenised. After increasing the temperature of the waxes to their melting temperature, the oil phase is added under stirring, and the mixture is homogenised for 5 minutes. Pigments and fragrances previously dispersed in castor oil are finally added, and the entire mass is vented, poured into moulds and cooled down.

EXAMPLE 2

| Care stick | |
|---|---|
| Isopropyl palmitate | 15.0 |
| Candelilla wax | 7 |
| Riz wax | 3 |
| Carnauba wax | 3.5 |
| Beeswax | 2.0 |
| Lanoline | 10.0 |
| Castor oil | ad 100 |
| Jojoba oil | 2.0 |
| α-tocopherol/cellulose complex with phosphatidylcholine | 8.0 |

EXAMPLE 2-continued

Care stick

| | |
|---|---|
| Glycerol | 5.0 |
| Food flavouring | 0.5 |
| Fragrances | 0.5 |

Processing is performed in the same manner as in Example 1.

What is claimed is:

1. A lipstick on a wax base, which contains vitamins, said lipstick further comprising an addition complex of:
   a cellulose derivative,
   a phospholipid and
   an α-tocopherol ester
wherein the cellulose derivative is provided in the form of micro-capsules or a mixture of micro-capsule and micro-capsule fragments.

2. A lipstick according to claim 1, wherein the α-tocopherol ester is α-tocopheryl acetate.

3. A lipstick on a wax base, which contains vitamins, said lipstick further comprising an addition complex of:
   a cellulose derivative,
   a phospholipid,
   an α-tocopherol ester and
   neral salts in an amount of from 1 to 2.5 g/l.

4. A lipstick according to claim 1, wherein the phospholipid is phosphatidylcholine.

5. A lipstick according to claim 1, wherein the proportion of the addition complex is 2 to 30 wt. % relative to the overall weight of said lipstick.

6. A lipstick according to claim 1, wherein the proportion of the addition complex is 5 to 25 wt. % relative to the overall weight of said lipstick.

7. A lipstick according to claim 1, further comprising additives selected from the group consisting of oil-soluble UVA and UVB filters.

8. A lipstick according to claim 1, further comprising additives selected from the group consisting of $TiO_2$, $SiO_2$, ZnO and mixtures thereof.

9. A lipstick on a wax base which contains vitamins, said stick comprising an addition complex of:
   a cellulose derivative selected from the group consisting of carboxymethyl cellulose, methyl cellulose, hydroxymethyl cellulose, hydroxypropyl cellulose and hydroxypropylmethyl cellulose, said derivative having particle sizes between 0.5 and 100 μm,
   a phospholipid and
   an α-tocopherol ester selected from the group consisting of α-tocopheryl acetate, -succinate, -propionate, -oleate, -linolate, -sorbate,
said addition complex comprising 0.5 to 40 wt. % of said lipstick,
said lipstick further comprising cosmetically conventional fats, waxes and additives having a proportion of 99.5 to 60 wt. % of said lipstick,
said lipstick being produced by a process comprising:
   dispersing said cellulose derivative in an oil phase while adding the phospholipid under stirring at 200 to 400 rpm at a temperature between 40 to 55° C.,
   adding the α-tocopherol ester in powdery form under stirring and increasing the temperature to 60 to 65° C.,
   homogenising the mixture at 10,000 to 15,000 rpm,
   adding fats, waxes and, optionally, further additives, and
   pouring the homogenised mixture at 60 to 80° C. into moulds,
   wherein the process is performed without adding an aqueous phase.

10. A lipstick as in claim 1, wherein said cellulose derivative is selected from the group consisting of carboxymethyl cellulose, methyl cellulose, hydroxymethyl cellulose, hydroxypropyl cellulose and hydroxypropylmethyl cellulose.

11. A lipstick as in claim 10, wherein said cellulose derivative when added has a particle size of between 0.5 and 100 μm.

12. A lipstick as in claim 1, wherein said α-tocopherol ester is selected from the group consisting of α-tocopheryl acetate, -succinate, -propionate, -oleate, -linolate, and -sorbate.

13. A lipstick as in claim 1, wherein said addition complex comprises 0.5 to 40 wt. % of the overall weight of said stick.

14. A lipstick as in claim 1, said lipstick comprising cosmetically acceptable fats, waxes and additives in an amount of 99.5 to 60 wt. % based on the overall weight of said stick.

15. A lipstick according to claim 7, wherein said oil-soluble UVA and UVB filters are selected from the group consisting of 4-aminobenzoic acid derivatives, cinnamic acid esters, benzo-phenone derivatives, 3-benzylidene camphor derivatives, salicylic acid derivatives, benzimidazol derivatives, and benzoylmethane derivatives.

* * * * *

UNITED STATES PATENT AND TRADEMARK OFFICE
CERTIFICATE OF CORRECTION

PATENT NO.   : 6,517,818 B1
DATED        : February 11, 2003
INVENTOR(S)  : Karin Golz-Berner, Leonhard Zastrow and Benoit Joly It is certified that error appears in the above-identified patent and that said Letters Patent is hereby corrected as shown below:

Title page,
Item [30], Foreign Application Priority Data, should read as follows:
-- Nov. 4, 1998 (DE) 198 52 196 --

Signed and Sealed this

Twenty-eighth Day of October, 2003

JAMES E. ROGAN
*Director of the United States Patent and Trademark Office*